(12) United States Patent
Ralph et al.

(10) Patent No.: US 7,722,646 B2
(45) Date of Patent: *May 25, 2010

(54) POLYAXIAL PEDICLE SCREW HAVING A ROTATING LOCKING ELEMENT

(75) Inventors: James D. Ralph, Seaside Park, NJ (US); Stephen Tatar, Montville, NJ (US)

(73) Assignee: K2M, Inc., Leesburg, VA (US)

( * ) Notice: Subject to any disclaimer, the term of this patent is extended or adjusted under 35 U.S.C. 154(b) by 594 days.

This patent is subject to a terminal disclaimer.

(21) Appl. No.: 11/010,593

(22) Filed: Dec. 13, 2004

(65) Prior Publication Data

US 2005/0119658 A1    Jun. 2, 2005

Related U.S. Application Data

(63) Continuation of application No. 10/115,747, filed on Apr. 3, 2002, now Pat. No. 6,840,940, which is a continuation of application No. 09/789,935, filed on Feb. 15, 2001, now Pat. No. 6,451,021.

(51) Int. Cl.
*A61B 17/70* (2006.01)

(52) U.S. Cl. .................. 606/246; 606/265; 606/300; 606/305

(58) Field of Classification Search .............. 606/54, 606/60, 61
See application file for complete search history.

(56) References Cited

U.S. PATENT DOCUMENTS

| 5,042,982 A |   | 8/1991 | Harms et al. | |
|---|---|---|---|---|
| 5,122,131 A | * | 6/1992 | Tsou | 606/328 |
| 5,176,678 A | * | 1/1993 | Tsou | 606/267 |
| 5,207,678 A | * | 5/1993 | Harms et al. | 606/267 |
| 5,281,222 A | * | 1/1994 | Allard et al. | 606/54 |
| 5,443,467 A |   | 8/1995 | Biedermann et al. | |
| 5,584,834 A |   | 12/1996 | Errico et al. | |
| 5,603,714 A | * | 2/1997 | Kaneda et al. | 606/272 |
| 5,662,653 A | * | 9/1997 | Songer et al. | 606/61 |
| 5,882,350 A | * | 3/1999 | Ralph et al. | 606/278 |
| 5,891,145 A |   | 4/1999 | Morrison et al. | |
| 6,010,503 A |   | 1/2000 | Richelsoph et al. | |

(Continued)

FOREIGN PATENT DOCUMENTS

WO    WO 9849960 A1 * 11/1998

*Primary Examiner*—Thomas C Barrett
*Assistant Examiner*—Nicholas Woodall
(74) *Attorney, Agent, or Firm*—Carter, DeLuca, Farrell & Schmidt, LLP

(57) ABSTRACT

A screw and coupling element assembly for use with an orthopedic rod implantation apparatus includes a screw with a head and a shaft extending from the head, a coupling element with a seat within which the head is seatable such that the shaft protrudes from the coupling element, and a locking element mateable with the coupling element and when mated is selectively movable through a plurality of positions including unlocked and locked positions. When in the unlocked position, the locking element presents a rod-receiving channel and the head is movable in the seat such that the shaft is directable in a plurality of angles relative to the coupling element. When in the locked position, a rod disposed within the rod-receiving channel is fixed relative to the coupling element and the head is immovable in the seat such that the shaft is fixed at an angle relative to the coupling element.

25 Claims, 8 Drawing Sheets

U.S. PATENT DOCUMENTS

| | | | |
|---|---|---|---|
| 6,086,588 A * | 7/2000 | Ameil et al. | 606/266 |
| 6,113,601 A | 9/2000 | Tatar | |
| 6,402,752 B2 | 6/2002 | Schaffler-Wachter et al. | |
| 6,451,021 B1 | 9/2002 | Ralph et al. | |
| 6,547,789 B1 * | 4/2003 | Ventre et al. | 606/61 |
| 6,565,565 B1 * | 5/2003 | Yuan et al. | 606/61 |
| 6,626,906 B1 * | 9/2003 | Young | 606/278 |
| 6,827,719 B2 * | 12/2004 | Ralph et al. | 606/272 |
| 6,840,940 B2 | 1/2005 | Ralph et al. | |

* cited by examiner

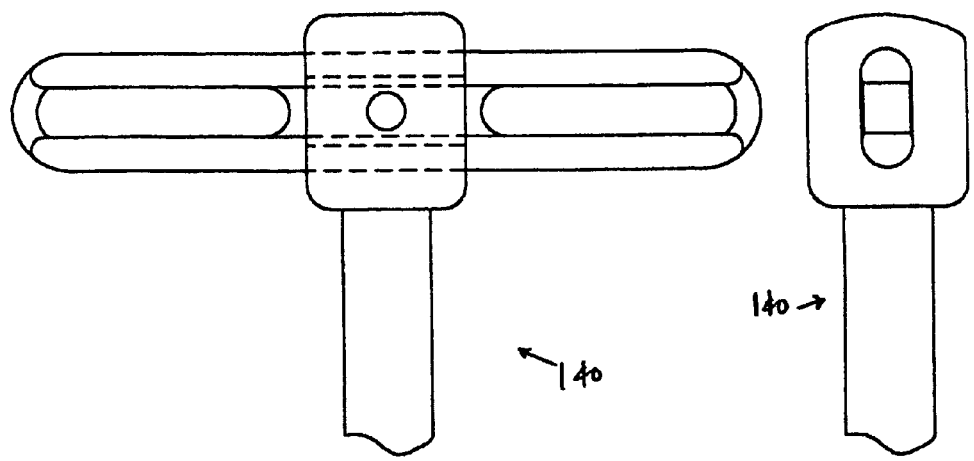
FIG. 4c
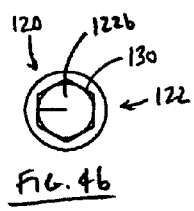
FIG. 4b
FIG. 4d
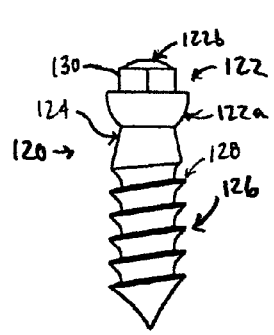
FIG. 4a
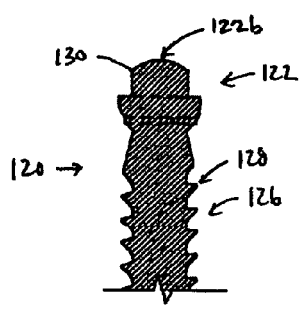
FIG. 4e

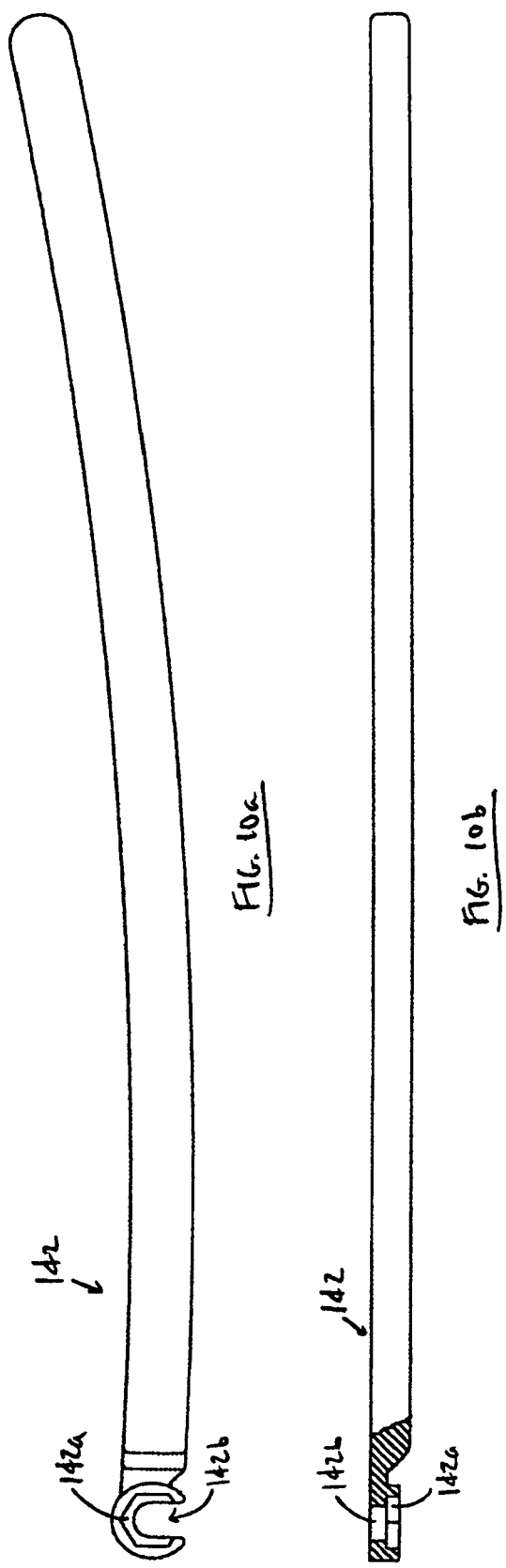

POLYAXIAL PEDICLE SCREW HAVING A ROTATING LOCKING ELEMENT

CROSS REFERENCE TO RELATED APPLICATION

This application is a continuation of U.S. patent application Ser. No. 10/115,747 entitled "Polyaxial Pedicle Screw Having a Rotating Locking Element", filed Apr. 3, 2002, now U.S. Pat. No. 6,840,940 which is a continuation of U.S. patent application Ser. No. 09/789,935, filed Feb. 15, 2001, now U.S. Pat. No. 6,451,021. The entire contents of each of these prior applications are hereby expressly incorporated by reference.

FIELD OF THE INVENTION

The invention relates generally to screws and coupling element assemblies for use with orthopedic fixation systems. More particularly, the invention relates to a screw and coupling element assembly, for use with an orthopedic rod implantation apparatus, that includes a locking element that simultaneously locks a head of the screw within a seat of the coupling element so that a shaft of the screw is fixed at an angle relative to the coupling element and a rod, of the orthopedic rod implantation apparatus, disposed within a rod-receiving channel of the locking element is fixed relative to the coupling element

BACKGROUND OF THE INVENTION

The bones and connective tissue of an adult human spinal column consists of more than twenty discrete bones coupled sequentially to one another by a tri-joint complex which consist of an anterior disc and the two posterior facet joints, the anterior discs of adjacent bones being cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine is the sacral bones (including the coccyx). The component bones of the cervical spine are generally smaller than those of the thoracic and lumbar spine.

Referring now to FIGS. 1, 2, and 3, top, side, and posterior views of a vertebral body, a pair of adjacent vertebral bodies, and a sequence of vertebral bodies are shown, respectively. The spinal cord is housed in the central canal 10, protected from the posterior side by a shell of bone called the lamina 12. The lamina 12 includes a rearwardly and downwardly extending portion called the spinous process 16, and laterally extending structures which are referred to as the transverse processes 14. The anterior portion of the spine comprises a set of generally cylindrically shaped bones which are stacked one on top of the other. These portions of the vertebrae are referred to as the vertebral bodies 20, and are each separated from the other by the intervertebral discs 22. The pedicles 24 comprise bone bridges which couple the anterior vertebral body 20 to the corresponding lamina 12.

The spinal column of bones is highly complex in that it includes over twenty bones coupled to one another, housing and protecting critical elements of the nervous system having innumerable peripheral nerves and circulatory bodies in close proximity. In spite of these complexities, the spine is a highly flexible structure, capable of a high degree of curvature and twist in nearly every direction. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the dassifications suggest, lateral and anterior assemblies are coupled to the anterior portion of the spine, which is the sequence of vertebral bodies. Posterior implants generally comprise pairs of rods, which are aligned along the axis which the bones are to be disposed, and which are then attached to the spinal column by either hooks which couple to the lamina or attach to the transverse processes, or by screws which are inserted through the pedicles.

"Rod assemblies" generally comprise a plurality of such screws which are implanted through the posterior lateral surfaces of the laminae, through the pedicles, and into their respective vertebral bodies. The screws are provided with upper portions which comprise coupling elements, for receiving and securing an elongate rod therethrough. The rod extends along the axis of the spine, coupling to the plurality of screws via their coupling elements. The rigidity of the rod may be utilized to align the spine in conformance with a more desired shape.

It has been identified, however, that a considerable difficulty is associated with inserting screws along a misaligned curvature and simultaneously exactly positioning the coupling elements such that the rod receiving portions thereof are aligned so that the rod can be passed therethrough without distorting the screws. Attempts at achieving proper alignment with fixed screws is understood to require increased operating time, which is known to enhance many complications associated with surgery. Often surgical efforts with such fixed axes devices cannot be achieved, thereby rendering such instrumentation attempts entirely unsuccessful.

The art contains a variety of attempts at providing instrumentation which permit a limited freedom with respect to angulation of the screw and the coupling element These teachings, however, are generally complex, inadequately reliable, and lack long-term durability. These considerable drawbacks associated with prior art systems also include difficulty in properly positioning the rod and coupling elements, and the tedious manipulation of the many parts that are used in the prior art to lock the rod, the screw, and the coupling element in position once they are properly positioned. It is not unusual for displacement to occur as these parts are manipulated to lock the elements, which is clinically unacceptable, and repeated attempts at locking the elements in proper position must be made to remedy this displacement.

There is, therefore, a need for a screw and coupling element assembly which provides a polyaxial freedom of implantation angulation with respect to rod reception. There is also a need for such an assembly which comprises a reduced number of elements, and which correspondingly provides for expeditious implantation. There is also a need for such an assembly that provides reduced difficulty in locking steps to prevent unwanted displacement of the elements prior to locking. There is also a need for an assembly which is reliable, durable, and provides long term fixation support.

SUMMARY OF THE INVENTION

The invention provides a screw and coupling element assembly for use with an orthopedic rod implantation apparatus. The assembly includes a securing element such as, for example, a screw, that has a head and a shaft that extends from the head. Preferably, the head has an engagement surface that can be engaged by a screwdriving tool. Preferably, the head also has a curvate proximal portion from which the shaft extends.

The screw and coupling element assembly further includes a coupling element and a locking element. The coupling element has a seat within which the head of the screw can be seated such that the shaft of the screw protrudes from the coupling element. The locking element can be mated with the coupling element and thereafter can be selectively moved through a plurality of positions including an unlocked position and a locked position. When the locking element is in the unlocked position, the locking element presents a rod-receiving channel and the head of the screw is movable in the seat of the coupling element, such that the shaft of the screw can be directed in a plurality of angles relative to the coupling element. When the locking element is in the locked position, a rod disposed within the rod-receiving channel is fixed relative to the coupling element, and the head of the screw is immovable in the seat of the coupling element, such that the shaft of the screw is fixed at an angle relative to the coupling element. More particularly, when the locking element is in the locked position, the locking element is compression locked within the coupling element, the head of the screw is compression locked within the seat of the coupling element, and the rod is compression locked within the rod-receiving channel.

Preferably, at least one feature on the locking element can be used to move the locking element through the positions when the locking element is disposed within the coupling element Preferably, the feature comprises an engagement surface that can be engaged by a corresponding surface of a tool, such that the tool can engage the engagement surface of the feature and effectively move the locking element. Preferably, the corresponding surface of the tool can engage the engagement surface of the feature despite the presence of the rod in the rod-receiving channel.

Preferably, the seat of the coupling element can be defined by a bore in the coupling element and a socket defined by a curvate volume adjacent the bore. The curvate volume corresponds to the curvate proximal portion of the head of the screw such that the curvate proximal portion can be nested in the socket. When the curvate proximal portion of the head of the screw is nested in the socket, the shaft of the screw protrudes from the bore and the curvate proximal portion cannot pass fully through the bore. When the locking element is in the unlocked position, the curvate proximal portion of the head of the screw can rotate and angulate in the socket such that the shaft of the screw can be directed through a range of angles relative to the coupling element. When the locking element is in the locked position, the curvate proximal portion of the head of the screw is immovable in the socket such that the shaft of the screw is fixed at an angle relative to the coupling element Preferably, the locking and unlocking action of the locking element is effected as follows. The head of the screw has a distal portion defined by a compression surface and the locking element has a permissive surface that is presented to the compression surface of the head of the screw when the locking element is in the unlocked position. When presented with the permissive surface of the locking element, the compression surface of the head of the screw is unhindered such that the head of the screw is movable in the seat of the coupling element. The locking element also has a confrontational surface that is presented to the compression surface of the head of the screw when the locking element is in the locked position. The confrontational surface of the locking element is defined by a recess that has a recessed surface corresponding to the compression surface of the head of the screw. Therefore, when the locking element is in the locked position: (1) the locking element is compressed within the coupling element, (2) the compression surface of the head of the screw is compressed by the confrontational surface of the locking element such that the curvate proximal portion of the head of the screw is compressed toward the bore of the coupling element and the head of the screw is immovable in the seat of the coupling element, and (3) the compression surface of the head of the screw seats in the recess of the confrontational surface and thereby is biased against retreat from the recess. The compression surface of the head of the screw can be a curvate surface and the confrontational surface of the locking element can extend from an edge of the permissive surface of the locking element and terminate in the recess of the confrontational surface. The confrontational surface of the locking element preferably becomes increasing confrontational and therefore is gradually presented to the compression surface of the head of the screw as the locking element is moved from the unlocked position to the locked position.

Preferably, the rod-receiving channel, presented by the locking element when the locking element is in the unlocked position, is defined by substantially parallel walls. When the locking element is in the locked position, the walls are compressed toward one another such that the rod is compressed within the channel and thereby fixed relative to the coupling element Preferably, the walls are increasingly compressed toward one another as the locking element is moved from the undocked position to the locked position.

Preferably, the coupling element has a bore that permits use of the screwdriving tool when the head is seated in the seat, allowing the screwdriving tool to engage the head as described above. Also preferably, the locking element has a bore that permits use of the screwdriving tool when the locking element is disposed within the coupling element in an unlocked position and the head is seated in the seat, allowing the screwdriving tool to engage the head as described above.

A use of the invention can be summarized as follows. First, the locking element is disposed within the coupling element. Then, the locking element is rotated within the coupling element until the locking element is in the unlocked position. The top bores of the locking element and the coupling element will then permit the insertion of the screw into the seat of the coupling element. The surgeon can freely rotate and angulate the screw in the socket to direct the shaft in the clinically appropriate direction for secure lodging in a vertebral bone.

Once the surgeon directs the shaft of the screw in the clinically appropriate direction, he passes the operative end of the screwdriving tool through the top bores to engage the head of the screw to rotate the screw and drive the shaft of the screw into the vertebral bone. A predrill hole is usually provided in the bone, into which it is desired that the screw be disposed.

Typically, the surgeon will repeat the process described above using additional screws, coupling elements, and locking elements, lodging the additional screws into the same vertebral bone or other vertebral bones, depending on the clinically desirable result To that end, the invention encompasses an orthopedic rod implantation apparatus having a plurality of screws and coupling elements of the types described above, and at least one elongate rod. Many implantations will require the use of two rods, however, only one rod or more than two rods may be necessary. The surgeon will, for example, lodge two screws into a first verterbal bone (the screws are positioned laterally adjacent one another in the same bone, one in each pedicle), and lodge two other screws into a second vertebral bone (the screws are positioned laterally adjacent one another in the same bone, one in each pedicle) that may be adjacent the first vertebral bone or may be separated from the first vertebral bone by other vertebral bones that are damaged or unstable.

In a healthy spine, each screw in one of the pairs would roughly align with the corresponding screw in the other pair, because the vertebral bones would be vertically aligned. However, in some cases, the screws will not be aligned because the spine is laterally crooked and the surgeon is installing the implant to realign the vertebral bones. Therefore, in such cases, once the screws are in place, and the associated coupling elements and locking elements are in the unlocked position, presenting respective rod-receiving channels, and free to rotate and angulate with respect to the head of the associated screw, the surgeon inserts a rod into one rod-receiving channel, and thereafter into another rod-receiving channel, so that the rod lines up the verterbral bones affected thereby in a clinically desirable manner, urging them, typically, into vertical alignment. The surgeon similarly inserts a second rod into the remaining two rod receiving channels to balance the alignment forces.

Once the rods are in the rod receiving channels, the surgeon proceeds to move each locking element into the locked position by rotating the locking element. As the locking element is moved to the locked position, the permissive surface, of the locking element, that is presented to the compression surface of the head of the screw when the locking element is in the unlocked position, is removed and the compression surface is increasingly presented with the confrontational surface. This causes the curvate proximal portion of the head of the screw to be increasingly compressed toward the bore until the head is immovable in the seat of the coupling element. Ultimately, the compression surface seats in the recess and thereby is biased against retreat from the recess. This prevents accidental reverse rotational slippage of the locking element from occurring and moving the locking element to the unlocked position.

In addition, as the locking element is moved to the locked position, the rod-receiving channel presented by the locking element when the locking element is in the unlocked position gradually closes. Ultimately, the channel is completely closed. This prevents the rod from laterally exiting the locking element Further, the walls of the channel are gradually compressed toward one another, until they ultimately secure the rod between them so that the rod is fixed relative to the coupling element. This prevents the rod from axially exiting the locking element.

In addition, as the locking element is moved to the locked position, the locking element itself is gradually compressed within the coupling element until it ultimately is secured within the coupling element. More specifically, as the rod seeks to radially force the walls and apart, the outer surface of the locking element seeks to radially push against the inner surface of the coupling element. However, the structural integrity of the coupling element resists the radial force of the locking element, and the locking element is secured in the coupling element thereby. This prevents the locking element from axially exiting the coupling element.

In this manner, once the locking element is moved to the locked position, the screw, the coupling element, the locking element, and the rod are all fixed relative to one another and to the bone. When all of the locking elements are so positioned, the implant is installed. After the surgeon moves all of the locking elements in the orthopedic rod implantation apparatus to the locked position, he closes the wounds of the patient and the surgery is complete.

Multiple screw and coupling element assemblies are generally necessary to complete the full array of anchoring sites for a rod immobilization system, however, the screw and coupling element assembly of the invention is designed to be compatible with alternative rod systems so that, where necessary, the invention may be employed to rectify the failures of other systems, the implantation of which may have already begun.

BRIEF DESCRIPTION OF THE DRAWINGS

FIGS. 4a, 4b and 4c are side, top, and cutaway side views of a screw suitable for use in the invention.

FIGS. 4d and 4e are side cutaway views of a screwdriving tool suitable for driving the screw of FIGS. 4a, 4b and 4c.

FIGS. 10a and 10b are front and side cutaway views of a wrenching tool suitable for wrenching hexagonal protrusions of the locking element of FIGS. 6a-e.

DETAILED DESCRIPTION OF THE INVENTION

Figure 2:
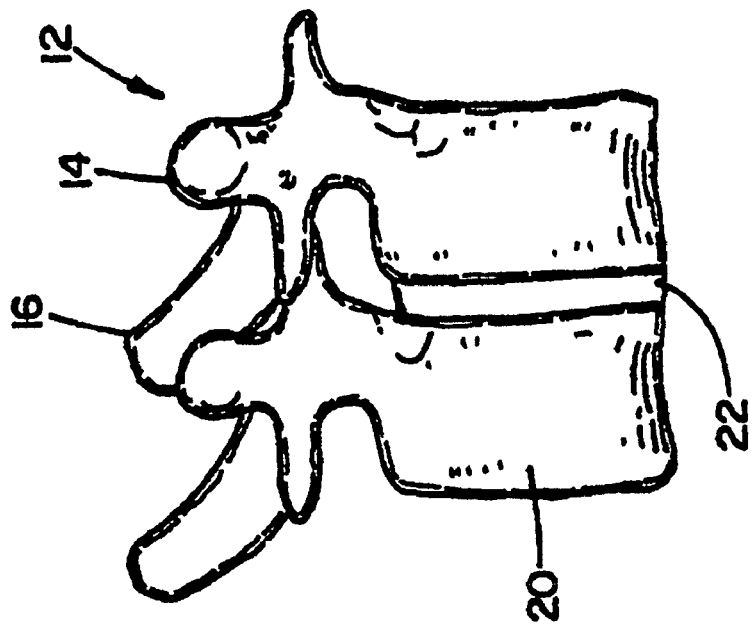
FIG. 2 is a side view of a pair of adjacent vertebrae of the type shown in FIG. 1.
Figure 1:
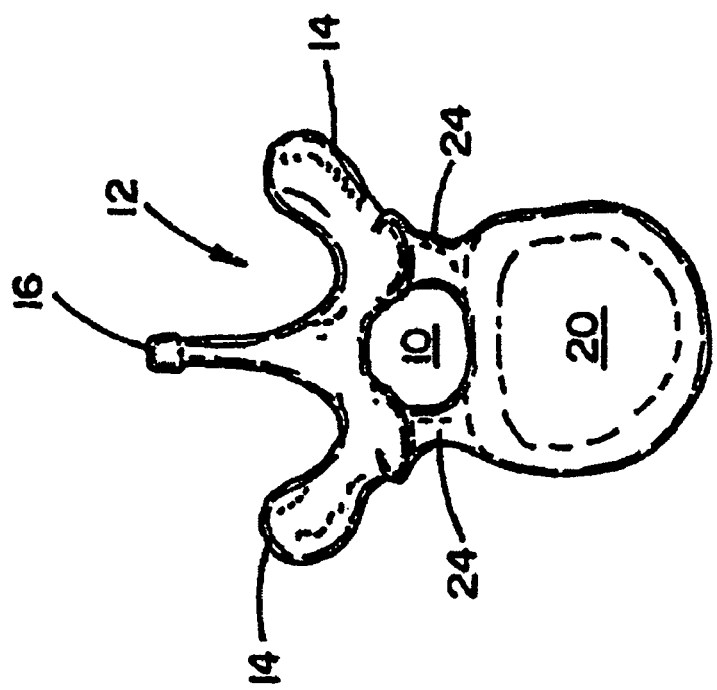
FIG. 1 is a top view of a human vertebra.
Figure 3:
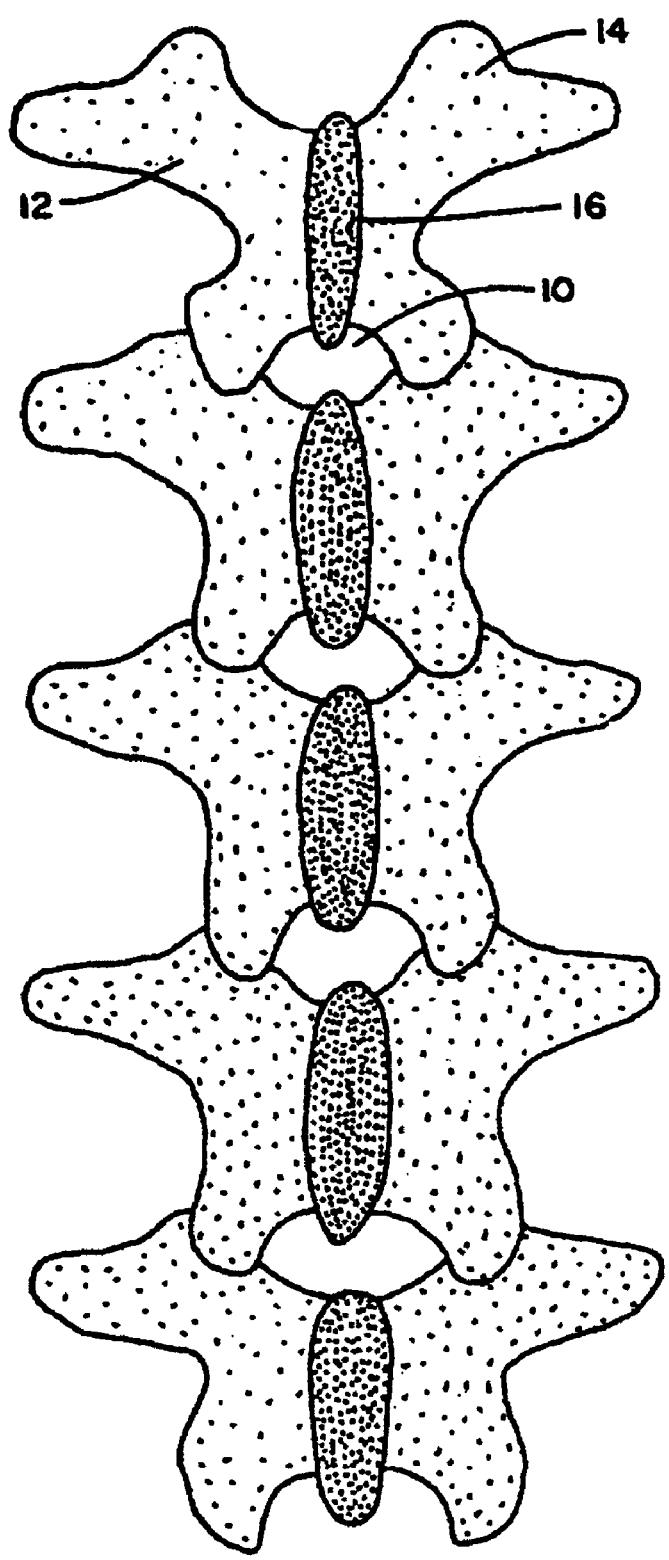
FIG. 3 is a posterior view of a sequence of vertebrae of the type shown in FIGS. 1 and 2.

While the invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the invention and not as limiting of such broad scope.

In an embodiment, the invention provides a screw and coupling element assembly for use with an orthopedic rod implantation apparatus. The assembly includes a securing element such as, for example, a screw, that has a head and a shaft that extends from the head. Other securing elements can include, for example, lamina hooks and sacral blocks.

Accordingly, FIG. 4a illustrates a side view of a screw 120 suitable for use in the invention. The screw 120 includes a head 122 and a shaft 126 that extends from the head 122. The shaft 126 is shown as having a tapered shape with a high pitch thread 128. It shall be understood that a variety of shaft designs are interchangeable with the screw of the invention. The specific choice of shaft features, such as thread pitch, shaft diameter to thread diameter ratio, and overall shaft shape, should be made be the physician with respect to the conditions of the individual patient's bone, however, the invention is compatible with a wide variety of shaft designs.

Preferably, the head has an engagement surface that can be engaged by a screwdriving tool. In this regard, one of the head and the tool can have a polygonal recess and the other of the head and the tool can have an external structure that fits within the recess.

Accordingly, referring again to FIG. 4a and also to FIGS. 4b-4e, the head 122 of the illustrated screw 120 includes a hexagonal engagement surface 130 that fits within a hexagonal recess 140a of a screwdriving tool 140. The surface 130 defines a receiving locus for the application of a torque for driving the screw 120 into a vertebral bone. Of course, the specific shape of the surface 130 may be chosen to cooperate with any suitable screwdriving tool. For example, the surface 130 may include an engagement surface of another shape, or a recess such as, for example, a slot for receiving a standard screwdriver, a hexagonally shaped hole for receiving an allen wrench, or a threading for a correspondingly threaded post. Preferably, the surface 130 is co-axial with the generally elongate axis of the screw 120 and, most particularly, the shaft 126. Having the axes of the surface 130 and the shaft 126 co-linear facilitates step of inserting the screw 120 into the bone.

Preferably, the head has a curvate proximal portion from which the shaft extends. The curvate proximal portion can be a semi-spherical shape, exhibiting an external contour that is equidistant from a center point of the head. When the head has an engagement surface that can be engaged by a screwdriving tool, it is preferable that the engagement surface does not disrupt the functionality of the curvate proximal portion as described herein.

Accordingly, referring also to FIG. 4a again, the head 122 of the illustrated screw 120 includes a hemisphere 122a as the curvate proximal portion. The use of the hemisphere 122a in this embodiment frees the hexagonal engagement surface 130 to effectively receive the hexagonal recess 140a of the screwdriving tool 140.

Further, the head 122 of the illustrated screw 120 is connected to the shaft 126 at a neck 124. The diameter of the head 122 is equal to the largest diameter of the shaft 126, and the neck 124 tapers to expose the operative portions of the curvate proximal portion 122a of the head 122. This configuration permits the screw 120 to swing through a variety of angles before its position is fixed, as described below. It should be noted that in other embodiments, the diameter of the shaft 126 can be less than or greater than the diameter of the head 122, and the neck 124 may be un-tapered or differently tapered.

In this embodiment, the screw and coupling element assembly further includes a coupling element and a locking element. The coupling element has a seat within which the head of the screw can be seated such that the shaft of the screw protrudes from the coupling element. The locking element can be mated with the coupling element and thereafter can be selectively moved through a plurality of positions including an unlocked position and a locked position. When the locking element is in the unlocked position, the locking element presents a rod-receiving channel and the head of the screw is movable in the seat of the coupling element, such that the shaft of the screw can be directed in a plurality of angles relative to the coupling element. When the locking element is in the locked position, a rod disposed within the rod-receiving channel is fixed relative to the coupling element, and the head of the screw is immovable in the seat of the coupling element, such that the shaft of the screw is fixed at an angle relative to the coupling element. More particularly, when the locking element is in the locked position, the locking element is compression locked within the coupling element, the head of the screw is compression locked within the seat of the coupling element, and the rod is compression locked within the rod-receiving channel. At least one feature on the locking element can be used to move the locking element through the positions when the locking element is disposed within the coupling element. Preferably, the feature comprises an engagement surface that can be engaged by a corresponding surface of a tool, such that the tool can engage the engagement surface of the feature and effectively move the locking element. Preferably, the corresponding surface of the tool can engage the engagement surface of the feature despite the presence of the rod in the rod-receiving channel.

Figure 5B:
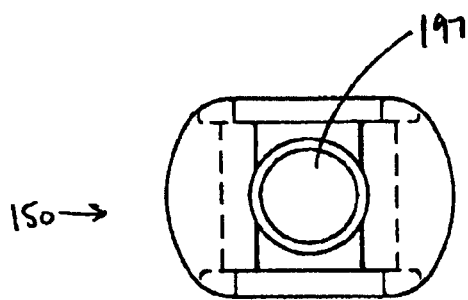
FIGS. 5a, 5b and 5c are front, side and top views of a coupling element suitable for use in the invention.
Figure 5A:
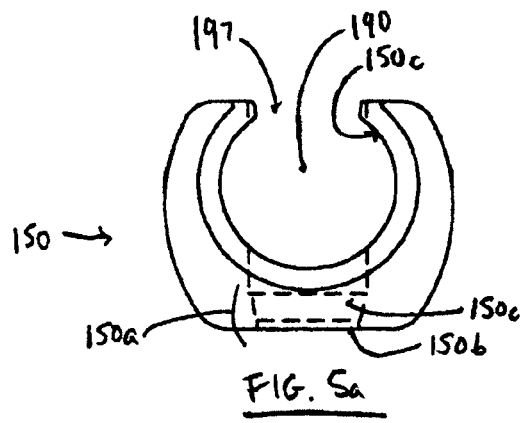
Figure 5C:
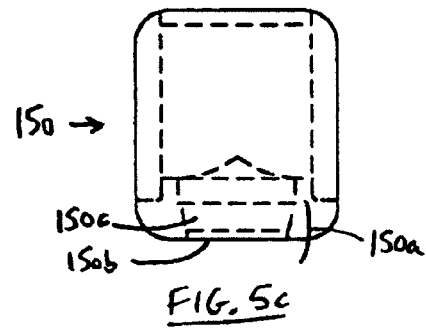
Figure 6E:
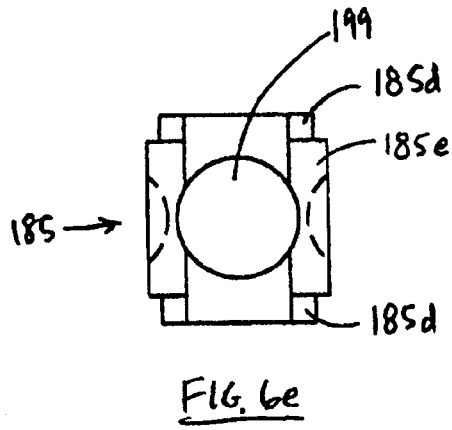
FIGS. 6a, 6b, 6c, 6d and 6e are front, side, front cutaway, side cutaway, and top views of a locking element suitable for use in the invention.
Figure 6B:
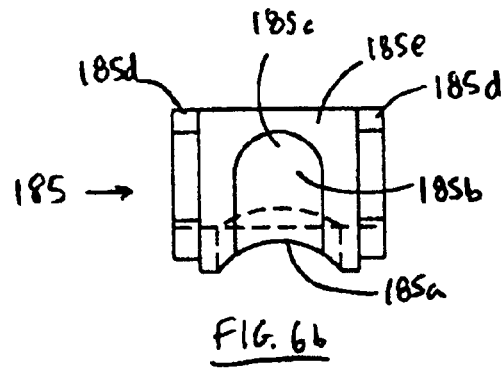
Figure 6A:
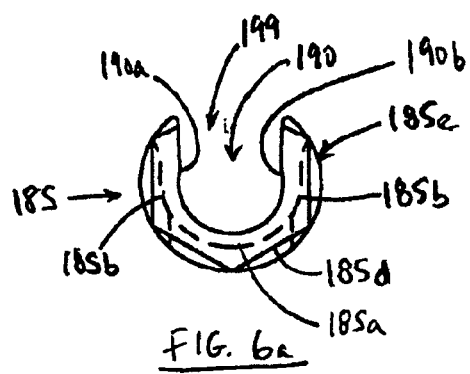
Figure 6D:
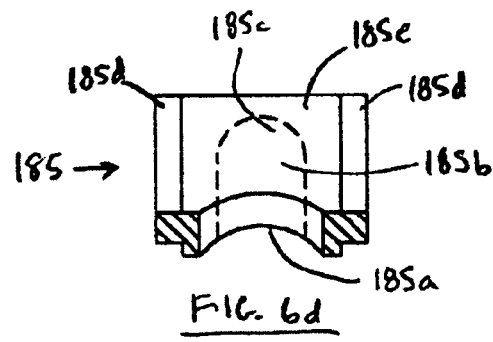
Figure 6C:
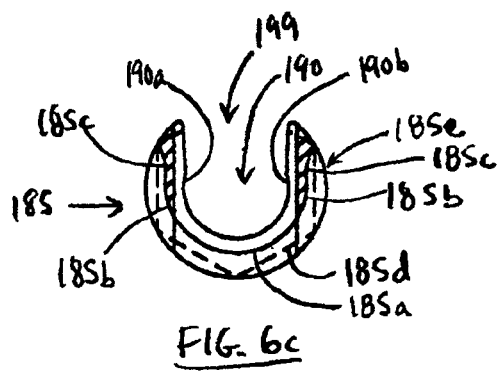
Figure 7:
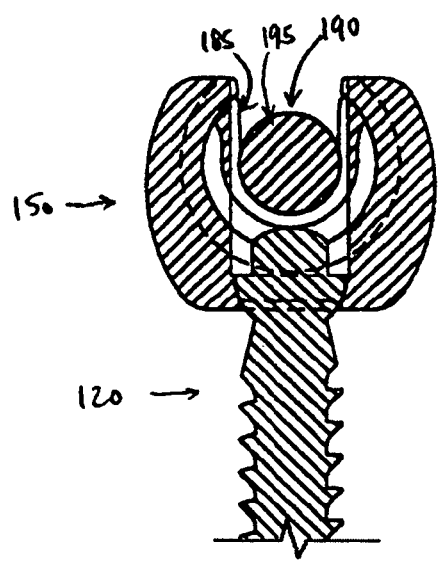
FIG. 7 is a front cutaway view of the screw of FIGS. 4a-c, the coupling element of FIGS. 5a-c, the locking element of FIGS. 6a-e, and a rod, with the locking element in an unlocked position.
Figure 8:
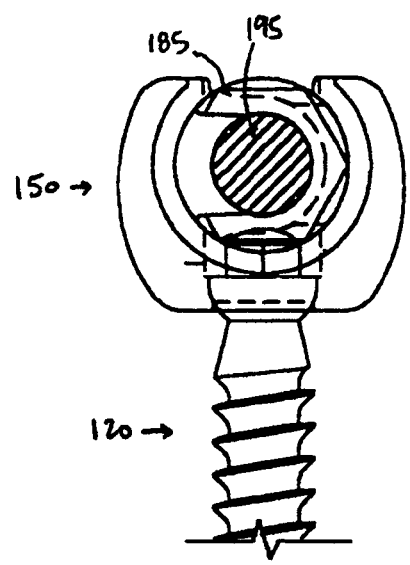
FIG. 8 is front view of the screw of FIGS. 4a-c, the coupling element of FIGS. 5a-c, the locking element of FIGS. 6a-e, and a rod, with the locking element in a locked position.
Figure 9:
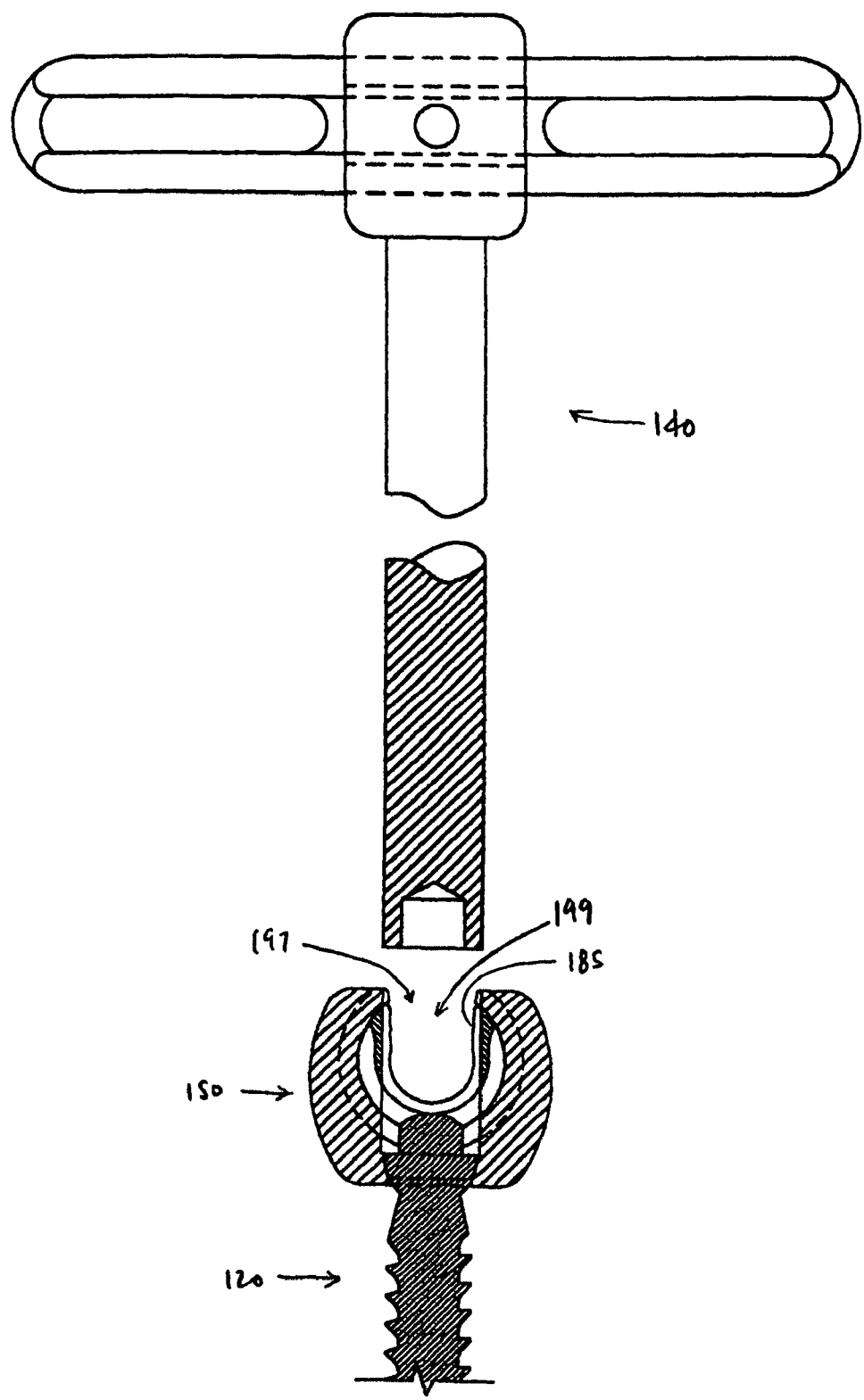
FIG. 9 is a side cutaway view of the screw of FIGS. 4a-c, the coupling element of FIGS. 5a-c, the locking element of FIGS. 6a-e, and the screwdriving tool of FIGS. 4d-e.

Accordingly, FIGS. 5a-c illustrate a coupling element 150 suitable for use in the invention, in front, top, side, front cutaway, and side cutaway views, respectively. FIGS. 6a-e illustrate a locking element 185 suitable for use in the invention, in front, top, and side views, respectively. FIG. 7 illustrates a front cutaway view of the screw 120 of FIG. 4, the coupling element 150, and the locking element 185 disposed within the coupling element 150 in an unlocked position. FIG. 8 illustrates a front view of the screw 120 of FIG. 4, the coupling element 150, and the locking element 185 disposed within the coupling element 150 in a locked position. The coupling element 150 has a substantially cylindrical inner surface 150c that accepts a cylindrical outer surface 185e of the locking element 185 for coaxial insertion and rotational translation therein so the locking element 185 can be rotated through a plurality of positions. At one extreme of the positional spectrum enjoyed by this locking element 185 is the unlocked position shown in FIG. 7. At the other extreme is the locked position shown in FIG. 8. In order to permit the locking element 185 to be moved through the positions, the locking element 185 has a feature on each end of the locking element 185, having a surface defined by a hexagonal protrusion 185d extending beyond a respective end of the coupling element 150. The hexagonal protrusions 185d can each be engaged by a corresponding surface of a tool such as, for example, the corresponding hexagonal recess 142a of the wrenching tool 142 shown in FIGS. 10a and 10b. So that the hexagonal recess 142a can engage the hexagonal protrusions 185d despite the presence of a rod 195 in a rod-receiving channel 190, the wrenching tool 142 has a slot 142b that accommodates the rod 195 as the wrenching tool 142 is rotated to rotate the locking element 185.

Preferably, the seat of the coupling element can be defined by a bore in the coupling element and a socket defined by a curvate volume adjacent the bore. The curvate volume corresponds to the curvate proximal portion of the head of the screw such that the curvate proximal portion can be nested in the socket. When the curvate proximal portion of the head of the screw is nested in the socket, the shaft of the screw protrudes from the bore, the curvate proximal portion cannot pass fully through the bore. When the locking element is in the unlocked position, the curvate proximal portion of the head of the screw can rotate and angulate in the socket such that the shaft of the screw can be directed through a range of angles relative to the coupling element. When the locking element is in the locked position, the curvate proximal portion of the head of the screw is immovable in the socket such that the shaft of the screw is fixed at an angle relative to the coupling element.

Accordingly, referring to FIGS. 5a-c, 6a-e and 7-8, a seat 150a of the illustrated coupling element 150 is defined by a bore 150b in the coupling element 150 and a socket defined by a curvate volume 150c adjacent the bore 150b. The curvate volume 150c corresponds to the curvate proximal portion 122a of the head 122 such that the curvate proximal portion 122a can be nested in the socket 150c. It is understood that the head 122 of the screw 120 is held within the curvate volume 150c by the relative size of the curvate proximal portion 122a as compared with the bore 150b. More specifically, the bore 150b has a diameter less than the diameter of the curvate proximal portion 122a. When the curvate proximal portion 122a is nested in the socket 150c, the shaft 126 protrudes from the bore 150a and the curvate proximal portion 122a cannot pass fully through the bore 150a. Further when the curvate proximal portion 122a is nested in the socket 150c, and when the locking element 185 is in the unlocked position, the curvate proximal portion 122a can rotate and angulate in the socket 150c such that the shaft 126 can be directed through a range of angles relative to the coupling element 150. Further when the curvate proximal portion 122a is nested in the socket 150c, and when the locking element 185 is in the locked position, the curvate proximal portion 122a is immovable in the socket 150c such that the shaft 126 is fixed at an angle relative to the coupling element 150.

Preferably, the locking and unlocking action of the locking element is effected as follows. The head of the screw has a distal portion defined by a compression surface and the locking element has a permissive surface that is presented to the compression surface of the head of the screw when the locking element is in the unlocked position. When presented with the permissive surface of the locking element, the compression surface of the head of the screw is unhindered such that the head of the screw is movable in the seat of the coupling element. The locking element also has a confrontational surface that is presented to the compression surface of the head of the screw when the locking element is in the locked position. The confrontational surface of the locking element is defined by a recess that has a recessed surface corresponding to the compression surface of the head of the screw. Therefore, when the locking element is in the locked position: (1) the locking element is compressed within the coupling element, (2) the compression surface of the head of the screw is compressed by the confrontational surface of the locking element such that the curvate proximal portion of the head of the screw is compressed toward the bore of the coupling element and the head of the screw is immovable in the seat of the coupling element, and (3) the compression surface of the head of the screw seats in the recess of the confrontational surface and thereby is biased against retreat from the recess. The compression surface of the head of the screw can be a curvate surface and the confrontational surface of the locking element can extend from an edge of the permissive surface of the locking element and terminate in the recess of the confrontational surface. The confrontational surface of the locking element preferably becomes increasing confrontational and therefore is gradually presented to the compression surface of the head of the screw as the locking element is moved from the unlocked position to the locked position.

Accordingly, referring to FIGS. 5a-c, 6a-e and 7-8, the illustrated head 122 has a distal portion defined by a compression surface 122b and the illustrated locking element 185 has a permissive surface 185a that is presented to the compression surface 122b when the locking element 185 is in the unlocked position. When presented with the permissive surface 185a, the compression surface 122b is unhindered such that the head 122 is movable in the seat 150a. Further, the illustrated locking element 185 has a confrontational surface 185b that is presented to the compression surface 122b when the locking element 185 is in the locked position. The confrontational surface 185b is defined by a recess 185c that has a recessed surface corresponding to the compression surface 122b. When the illustrated locking element 185 is in the locked position, (1) the locking element 185 is compressed within the coupling element 150, (2) the compression surface 122a is compressed by the confrontational surface 185b such that the curvate proximal portion 122a of the head 122 is compressed toward the bore 150b and the head 122 is immovable in the seat 150a, and (3) the compression surface 122b seats in the recess 185c and thereby is biased against retreat from the recess 185c. The illustrated compression surface 122a is a curvate surface and the confrontational surface 185b extends from an edge of the permissive surface 185a and terminates in the recess 185c. The confrontational surface 185b is tapered to become increasing confrontational as the locking element 185 is moved from the unlocked position to the locked position and therefore is gradually presented to the compression surface 122a as the locking element 185 is moved from the unlocked position to the locked position.

Preferably, the rod-receiving channel, presented by the locking element when the locking element is in the unlocked position, is defined by substantially parallel walls. When the locking element is in the locked position, the walls are compressed toward one another such that the rod is compressed within the channel and thereby fixed relative to the coupling element. Preferably, the walls are increasingly compressed toward one another as the locking element is moved from the unlocked position to the locked position.

Accordingly, referring to FIGS. 5a-c, 6a-e and 7-8, the rod-receiving channel 190 that is presented by locking element 185 when the locking element 185 is in the unlocked position has substantially parallel walls 190a, 190b. As the locking element 185 is moved from the unlocked position to the locked position, the walls 190a, 190b are increasingly compressed toward one another. When the locking element 185 is in the locked position, the walls 190a, 190b are compressed toward one another such that the rod 195 is compressed within the channel 190 and thereby fixed relative to the coupling element 150.

Preferably, the coupling element has a bore that permits use of the screwdriving tool when the head is seated in the seat, allowing the screwdriving tool to engage the head as described above. Also preferably, the locking element has a bore that permits use of the screwdriving tool when the locking element is disposed within the coupling element in an unlocked position and the head is seated in the seat, allowing the screwdriving tool to engage the head as described above.

Accordingly, with reference also to FIGS. 5a-c, 6a-e, 7 and 8, FIG. 9 illustrates a side cutaway view of the screw 120, coupling element 150, locking element 185, and screwdriving tool 140. It can be seen that a top surface of the coupling element 150 has a bore 197 through which the screwdriving tool 140, which is used to insert the screw 120 into the bone, may access and rotate the screw 120 through the coupling element 150. It can also be seen that a top surface of the locking element 150 has a bore 199 through which the screwdriving tool 140 may access and rotate the screw 120 through the locking element 185 when the locking element 185 is in the unlocked position.

Referring now to FIGS. 5a-c, 6a-e, 7-9 and 10a-10b, the preferred method of implantation and assembly is described hereinbelow. First, the locking element 185 is disposed within the coupling element 150 so that it can be selectively moved. This can be accomplished by coaxially inserting the locking element 185 into the coupling element 150, contacting the cylindrical outer surface of the locking element 185 with the substantially cylindrical inner surface 150c of the coupling element 150.

Once the locking element 185 is disposed within the coupling element 150 in this manner, the wrenching tool 142 shown in FIGS. 10a-10b can be used to engage the hexagonal protrusions 185d of the locking element 185 and rotate the locking element 195 within the coupling element 150 until the locking element 185 is in the unlocked position as shown in FIG. 7.

When the locking element 185 is in the unlocked position, the bore 199 of the locking element and the bore 197 of the coupling element permit the insertion of the screw 120 into the seat 150a. More particularly, the surgeon can pass the shaft 126 of the screw 120 and the head 122 of the screw through the bores 199 and 197, but only the shaft 126 will pass through the bore 150b of the coupling element 150. As stated above, the curvate proximal portion 122a of the head 122 will not pass through the bore 150b, but instead will nest in the seat 150a in the curvate volume 150c of the coupling element 150. The surgeon is then able to freely rotate and angulate the screw 120 in the socket 150c to direct the shaft 126 in the clinically appropriate direction for secure lodging in a vertebral bone.

It should be noted that while the insertion of the locking element 185 into the coupling element 150 and the subsequent insertion of the screw 120 through the bores 199 and 197 has been described, it is possible to pre-assemble these elements in this configuration prior to delivery to the surgeon to minimize the effort and time required from the surgeon in preparing the elements for operative use.

Once the surgeon directs the shaft 126 of the screw 120 in the clinically appropriate direction, he is able to pass the operative end of the screwdriving tool 140 shown in FIGS. 4d and 4e through the bore 199 and the bore 197 to engage the hexagonal engagement surface 130 of the head 122 of the screw 120. As stated above, the operative end of the screwdriving tool 140 has a hexagonal recess 140a for engaging the hexagonal engagement surface 130 and rotating the screw 120 to drive the shaft 126 of the screw 120 into the vertebral bone. A pre-drill hole is usually provided in the bone, into which it is desired that the screw 120 be disposed. The hole may be pre-tapped, or the external threading 128 of the screw 120 may include a self-tapping edge.

Typically, the surgeon will repeat the process described above using additional screws, coupling elements, and locking elements, lodging the additional screws into the same vertebral bone or other vertebral bones, depending on the clinically desirable result. To that end, the invention encompasses an orthopedic rod implantation apparatus having a plurality of screws and coupling elements of the types described above, and at least one elongate rod. Many implantations will require the use of two rods, however, only one rod or more than two rods may be necessary. The surgeon will, for example, lodge two screws into a first verterbal bone (the screws are positioned laterally adjacent one another in the same bone, one in each pedicle), and lodge two other screws into a second vertebral bone (the screws are positioned laterally adjacent one another in the same bone, one in each pedicle) that may be adjacent the first vertebral bone or may be separated from the first vertebral bone by other vertebral bones that are damaged or unstable.

In a healthy spine, each screw in one of the pairs would roughly align with the corresponding screw in the other pair, because the vertebral bones would be vertically aligned. However, in some cases, the screws will not be aligned because the spine is laterally crooked and the surgeon is installing the implant to realign the vertebral bones. Therefore, in such cases, once the screws are in place, and the associated coupling elements and locking elements are in the unlocked position, presenting respective rod-receiving channels, and free to rotate and angulate with respect to the head of their associated screw, the surgeon inserts a rod into one rod-receiving channel, and thereafter into another rod-receiving channel, so that the rod lines up the verterbral bones affected thereby in a clinically desirable manner, urging them, typically, into vertical alignment The surgeon similarly inserts a second rod into the remaining two rod receiving channels to balance the alignment forces.

Once the rods are in the rod receiving channels, the surgeon proceeds to move each locking element 185 into the locked position shown in FIG. 8. The surgeon uses the wrenching tool 142 shown in FIGS. 10a and 10b; engaging the hexagonal recess 142a of the wrenching tool 142 with one of the hexagonal protrusions 185d of the locking element and moving the wrenching tool 142 to rotate the hexagonal protrusion 185d and thereby rotate the locking element 185. As the locking element 185 is moved to the locked position, the permissive surface 185a, of the locking element 185, that is presented to the compression surface 122b of the head 122 when the locking element 185 is in the unlocked position, is removed and the compression surface 122b is increasingly presented with the confrontational surface 185b. This causes the curvate proximal portion 122a of the head 122 to be increasingly compressed toward the bore 150b until the head 122 is immovable in the seat 150a. Ultimately, the compression surface 122b seats in the recess 185c and thereby is biased against retreat from the recess 185. This prevents accidental reverse rotational slippage of the locking element 185 from occurring and moving the locking element to the unlocked position. The locking element 185 can still be moved back to the unlocked position if the surgeon desires to correct an error or to readjust the components, if the surgeon uses the wrenching tool 142 and applies enough force to overcome the force that seats the compression surface 122b in the recess 185c.

In addition, as the locking element 185 is moved to the locked position, the rod-receiving channel 190, presented by the locking element 185 when the locking element 185 is in the unlocked position, gradually doses. Ultimately, the channel 190 is completely dosed. This prevents the rod 195 from laterally exiting the locking element 185. Further, the walls 190a and 190b of the channel 190 are gradually compressed toward one another, until they ultimately secure the rod 195 between them so that the rod 195 is fixed relative to the coupling element 150. This prevents the rod 195 from axially exiting the locking element 185.

In addition, as the locking element 185 is moved to the locked position, the locking element 185 itself is gradually compressed within the coupling element 150 until it ultimately is secured within the coupling element 150. More specifically, as the rod 195 seeks to radially force the walls 190a and 190b apart, the outer surface of the locking element 185 seeks to radially push against the inner surface 150c of the coupling element 150. However, the structural integrity of the coupling element 150 resists the radial force of the locking element 185, and the locking element 185 is secured in the coupling element 150 thereby. This prevents the locking element 185 from axially exiting the coupling element 150.

In this manner, once the locking element 185 is moved to the locked position, the screw 120, the coupling element 150, the locking element 185, and the rod 195 are all fixed relative to one another and to the bone. When all of the locking elements 185 are so positioned, the implant is installed. After the surgeon moves all of the locking elements in the orthopedic rod implantation apparatus to the locked position, he closes the wounds of the patient and the surgery is complete.

While there has been described and illustrated embodiments of a screw and coupling element assembly, for use with an orthopedic rod implantation apparatus, it will be apparent to those skilled in the art that variations and modifications are possible without deviating from the broad spirit and principle of the invention. The invention shall, therefore, be limited solely by the scope of the claims appended hereto.

What is claimed is:

1. A spinal implant apparatus affixable to bone comprising:
a coupling element including a first compression surface;
a screw, the screw having a head with a curvate portion and a shaft extending from the curvate portion, wherein the head of the screw provides the first compression surface and the coupling element further includes a seat for receiving the head such that the shaft protrudes from the coupling element, wherein the seat is defined by a bore in the coupling element and further includes a socket defined by a curvate volume adjacent the bore, that corresponds to the curvate proximal portion such that the head nests in the socket and the shaft protrudes from the bore; and
a locking element rotatably disposed in the coupling element and selectively rotatable through a plurality of positions including an unlocked position and a locked position, the locking element being rotatably disposed in the coupling element in each position of the plurality of positions such that,
when the locking element is in the unlocked position, the head of the screw is movable in the socket, the shaft of the screw is positionable relative to the coupling element, and an opening of the locking element presents a rod-receiving channel; and
when the locking element is in the locked position, the head of the screw is fixed in the socket, the shaft of the screw is fixed relative to the coupling element, and a rod disposed within the rod-receiving channel is fixed relative to the coupling element wherein,
as the locking element rotates from the unlocked position to the locked position, a confrontational surface of the locking element increasingly engages the first compression surface such that opposing walls of the rod-receiving channel are compressed towards each other and increasingly engage the rod for fixing the rod relative to the coupling element.

2. The apparatus of claim 1, wherein the head has an engagement surface and the apparatus has a bore that permits access to the engagement surface when the head is in the seat.

3. The apparatus of claim 1, wherein:
the head has a distal portion defining the first compression surface; and
the locking element has a permissive surface and a confrontational surface, the confrontational surface being defined by a recessed surface corresponding to the first compression surface such that,
when the locking element is in the unlocked position, the permissive surface is in substantial alignment with the first compression surface and the head is movable in the seat; and
when the locking element is in the locked position, the confrontational surface engages the first compression surface for compressing the curvate proximal portion towards the bore such that the head is fixed in the seat and the first compression surface is seated in the confrontational surface for compressing the locking element within the coupling element.

4. The apparatus of claim 3, wherein the first compression surface is a curvate surface and the confrontational surface extends from an edge of the permissive surface to terminate in the recess and increasingly engages the first compression surface as the locking element is rotated from the unlocked position to the locked position.

5. An orthopedic rod implantation apparatus comprising:
at least one elongate rod; and
a plurality of coupling element assemblies, wherein at least one of the assemblies comprises:
a coupling element including a first compression surface;
a plurality of screws, at least one screw includes a head and a shaft extending therefrom, the head provides the first compression surface and the coupling element includes a seat for receiving the head such that the shaft protrudes from the coupling element, the head has an engagement surface and the apparatus has a bore that permits access to the engagement surface when the head is in the seat, and at least one screw is disposed in the coupling element; and
a locking element rotatably disposed in the coupling element and selectively rotatable through a plurality of positions including an unlocked position and a locked position, the locking element remaining disposed in the coupling element throughout its rotation such that,
when the locking element is in the unlocked position, the locking element and the coupling element together define a U-shaped rod-receiving channel having an open end opposite the screw; and
when the locking element is in the locked position, the rod, if disposed within the rod-receiving channel, is fixed relative to the coupling element wherein:
as the locking element rotates from the unlocked position to the locked position, a confrontational surface of the locking element increasingly engages the first compression surface such that the rod-receiving channel increasingly engages the rod for fixing the rod relative to the coupling element.

6. The apparatus of claim 5, wherein:
the head has a distal portion defining the compression surface;
the locking element has a permissive surface and a confrontational surface, the confrontational surface defined by a recessed surface corresponding to the first compression surface such that,
when the locking element is in the unlocked position, the permissive surface is in substantial alignment with the first compression surface and the head is movable in the seat; and
when the locking element is in the locked position, the confrontational surface engages the first compression surface for compressing the curvate proximal portion towards the bore such that the head is fixed in the seat and the first compression surface is seated in the confrontational surface for compressing the locking element within the coupling element.

7. The apparatus of claim 6, wherein the first compression surface is a curvate surface, the confrontational surface extends from an edge of the permissive surface to terminate in the recess and increasingly engages the first compression surface as the locking element is rotated from the unlocked position to the locked position.

8. The apparatus of claim 5, wherein the rod-receiving channel is defined by substantially parallel walls that are compressed towards one another when the locking element is in the locked position such that the rod is compressed within the channel and fixed relative to the coupling element.

9. An orthopedic rod implantation apparatus comprising:
at least one elongate rod; and
a plurality of coupling element assemblies, wherein at least one of the assemblies comprises:
 a coupling element including a first compression surface;
 a plurality of screws, at least one screw includes a head and a shaft extending therefrom, the head provides the first compression surface and the coupling element includes a seat for receiving the head such that the shaft protrudes from the coupling element, and at least one screw is disposed in the coupling element; and
 a locking element rotatably disposed in the coupling element and selectively rotatable through a plurality of positions including an unlocked position and a locked position, the locking element remaining disposed in the coupling element throughout its rotation such that,
 when the locking element is in the unlocked position, the locking element and the coupling element together define a U-shaped rod-receiving channel having an open end opposite the screw; and
 when the locking element is in the locked position, the rod, if disposed within the rod-receiving channel, is fixed relative to the coupling element wherein:
  as the locking element rotates from the unlocked position to the locked position, a confrontational surface of the locking element increasingly engages the first compression surface such that the rod-receiving channel increasingly engages the rod for fixing the rod relative to the coupling element;
wherein:
the head has a curvate proximal portion from which the shaft extends;
the seat is defined by a bore in the coupling element; and
the apparatus further includes a socket being defined by a curvate volume adjacent the bore that corresponds to the curvate proximal portion such that the head nests in the socket and the shaft protrudes from the bore such that,
 when the locking element is in the unlocked position the head is movable in the socket and the shaft is positionable relative to the coupling element; and
 when the locking element is in the locked position, the head is fixed in the socket and the shaft is fixed relative to the coupling element.

10. A locking assembly, comprising:
a securing element having a first compression surface;
a coupling element having a seat for receiving the securing element; and
a locking element rotatably disposed in the coupling element and selectively rotatable through a plurality of positions including an unlocked position and a locked position, the locking element remaining rotatably disposed in the coupling element as it rotates through the plurality of positions such that,
 when the locking element is in the unlocked position, the locking element and the coupling element define a U-shaped channel for receiving a rod, the opening of the U-shaped channel being opposite the seat of the coupling element and co-axial to the securing element in at least one position of the securing element; and
 when the locking element is in the locked position, the rod, if disposed within the channel, is fixed relative to the coupling element wherein:
  as the locking element rotates from the unlocked position to the locked position, a confrontational surface of the locking element increasingly engages the first compression surface of the securing element such the rod-receiving channel increasingly engages the rod for fixing the rod relative to the coupling element.

11. The assembly of claim 10, wherein when the locking element is in the locked position the locking element is compression locked within the coupling element, the securing element is compression locked within the seat, and the rod, if disposed within the channel, is compression locked within the channel.

12. The assembly of claim 11, wherein:
a bore in the coupling element and a socket adjacent the bore define the seat;
the securing element includes a head and a shaft, wherein the securing element is positionable in the socket such that the shaft protrudes from the bore;
the locking element has an increasingly confrontational surface terminating in a recessed surface; and
the channel is defined by walls of the locking element such that when the locking element is rotated from the unlocked position to the locked position;
 the locking element is compressed within the coupling element and compresses the walls towards one another such that the rod, if disposed within the channel, is compressed within the channel for fixing the rod relative to the coupling element; and
 the confrontational surface engages the first compression surface for compressing the head towards the bore and fixing the head in the socket.

13. The assembly of claim 10, wherein the locking element is provided with at least one engagement surface for engaging a tool, the tool being adapted to rotate the locking element through the plurality of positions.

14. A spinal implant apparatus configured and dimensioned to be attached to bone comprising:
a coupling element;
a screw disposed in the coupling element; and
a locking element rotatably disposed in the coupling element, said locking element defining a rod receiving channel having a first axis corresponding to a longitudinal axis of a non-threaded rod having a substantially smooth outer surface to be received therein;
wherein the locking element rotates about an axis concentric to said first axis between a locked position in which the non-threaded rod is fixed relative to the apparatus and an unlocked position in which the locking element cooperates with the coupling element and defines a U-shaped channel with an open end in coaxial alignment with an opening of a seat of the coupling element, said locking element remaining rotatably disposed in the coupling element as it rotates between the unlocked position and the locked position.

15. A spinal implant apparatus configured and dimensioned to be attached to bone, said apparatus including a coupling element for receiving a rod, said rod defining a longitudinal axis, and a screw disposed in the coupling element wherein the improvement comprises a locking element rotatably disposed in said coupling element, said locking element being rotatable about an axis concentric to said longitudinal axis of the rod between a locked position in which the rod is fixed relative to the apparatus and an unlocked position in which an opening of the locking element cooperates with an opening of the coupling element to define a U-shaped rod-receiving channel having an open end in axial alignment with a longitudinal axis of the screw in at least one position of the screw.

16. A spinal implant apparatus affixable to bone comprising:
- a coupling element having an axis;
- at least one screw being disposed in the coupling element;
- a locking element rotatably disposed in said coupling element and selectively rotatable within the coupling element from a first position defining an open rod receiving channel having an open end that is in axial alignment with a longitudinal axis of the at least one screw in at least one position of the at least one screw through a second position defining a partially open rod receiving channel to a third position defining a closed rod receiving channel, such that
  - when the locking element is in the first position, a rod is receivable in the rod receiving channel,
  - when the locking element is in the second position, the partially open rod receiving channel is smaller than a diameter of the rod, and
  - when the locking element is in the third position, the rod disposed in said rod receiving channel is fixed relative to the coupling element, the locking element being rotatably disposed in the coupling element as it rotates between the first unlocked position and the second locked position.

17. The spinal implant apparatus according to claim 16, wherein said locking element frictionally engages said rod in said locked position.

18. The spinal implant apparatus according to claim 16, wherein a rod disposed in said rod receiving channel defines an axis, and said locking element is rotatable about said axis.

19. The spinal implant apparatus of claim 16, wherein when the locking element is in the first position, the rod receiving channel is U-shaped and when the locking element is in the second position, the opening of the U-shaped rod receiving channel has a width that is less than the diameter of the rod.

20. The spinal implant apparatus according to claim 16, wherein when the locking element is in the second position, an open end of the partially open rod receiving channel is smaller than the diameter of the rod.

21. A spinal implant apparatus affixable to bone comprising:
- a screw having a head and a threaded shaft extending therefrom;
- a coupling element having an opening therethrough configured and dimensioned to permit the threaded shaft of the screw to extend through the opening with the screw head disposed within the coupling element; and
- a locking element rotatably disposed in the coupling element and having a camming surface, said locking element being selectively rotatable from a first position in which an opening of the locking element and an opening of the coupling element together define a U-shaped rod receiving channel having an open end opposite to the screw that is in axial alignment with a longitudinal axis of the screw to a second position with a rod disposed in said rod receiving channel such that said locking element camming surface engages the rod to fix the rod relative to the coupling element, the locking element being rotatably disposed in the coupling element as it rotates between the first position and the second position.

22. The spinal implant apparatus of claim 21, wherein the locking element is rotatable to a position between the first position and the second position such that the U-shaped channel presents an opening that has a width that is less than a diameter of the rod.

23. A spinal implant apparatus affixable to bone comprising:
- a screw having a head and a threaded shaft extending therefrom;
- a coupling element having an opening therethrough configured and dimensioned to permit the threaded shaft of the screw to extend through the opening with the screw head disposed within the coupling element, the shaft of the screw repositionable through a variety of angles relative to the coupling element;
- a locking element rotatably disposed in the coupling element and having opposing walls, said locking element being selectively rotatable from a first position presenting a rod receiving channel to a second position, the locking element being rotatably disposed in the coupling element as the locking element rotates between the first position and the second position, the shaft of the screw has a fixed angle relative to the coupling element when the locking element is in the second position; and
- a rod disposed in said rod receiving channel, said opposing walls of said locking element compressed towards each other, thereby fixing said rod relative to said coupling element when said locking element is in said second position;
- wherein rotating said locking element from said first position to said second position causes a camming surface thereof to contact said rod, thereby urging said rod toward said screw head.

24. The apparatus according to claim 23, wherein said screw has screw driving hole.

25. The apparatus according to claim 23, wherein said screw may be disposed at various angles relative to said coupling element with said locking element in said first position.

* * * * *